US012669473B2

(12) United States Patent
Stegemann et al.

(10) Patent No.: US 12,669,473 B2
(45) Date of Patent: *Jun. 30, 2026

(54) RESONANT ACOUSTIC RHEOMETRY FOR CHARACTERIZATION OF SOFT VISCOELASTIC MATERIALS

(71) Applicant: REGENTS OF THE UNIVERSITY OF MICHIGAN, Ann Arbor, MI (US)

(72) Inventors: Jan P. Stegemann, Ann Arbor, MI (US); Cheri X. Deng, Ann Arbor, MI (US); Eric C. Hobson, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 746 days.

This patent is subject to a terminal disclaimer.

(21) Appl. No.: 18/154,348

(22) Filed: Jan. 13, 2023

(65) Prior Publication Data

US 2023/0228715 A1      Jul. 20, 2023

Related U.S. Application Data

(60) Provisional application No. 63/299,846, filed on Jan. 14, 2022.

(51) Int. Cl.
*G01N 29/02*          (2006.01)
*G01N 29/04*          (2006.01)
(Continued)

(52) U.S. Cl.
CPC ............. *G01N 29/02* (2013.01); *G01N 29/04* (2013.01); *G01N 33/02* (2013.01);
(Continued)

(58) Field of Classification Search
CPC ........ G01N 29/02; G01N 29/04; G01N 33/02; G01N 33/483; G01N 33/487
See application file for complete search history.

(56) References Cited

U.S. PATENT DOCUMENTS 6,596,239 B2     7/2003   Williams et al.
6,925,856 B1     8/2005   Williams
(Continued)

OTHER PUBLICATIONS

Corey et al., Sonic Estimation of Elasticity via Resonance: A New Method of Assessing Hemostasis, Ann. Biomed. Eng., 44(5):1405-1424 (2016).

(Continued)

*Primary Examiner* — Kristina M Deherrera
*Assistant Examiner* — Gedeon M Kidanu
(74) *Attorney, Agent, or Firm* — MARSHALL, GERSTEIN & BORUN LLP

(57)          ABSTRACT

Techniques for performing an acoustic rheology measurement of a sample are provided. A first set of acoustic pulses is provided by a focused ultrasound transducer to induce surface oscillations of the sample. A second set of acoustic pulses is provided by a detection transducer to interrogate the sample and detect the echo pulses reflected by the sample surface as a function of time. The detection ultrasound transducer system converts the echo signals to an electrical signal associated with the detected echo pulses, and a processor determines a dynamic displacement of the interface of the sample as a function of time. The processor also determines the spectrum, resonant surface oscillation frequency, and damping coefficient. Viscoelastic properties of the material are determined from these measurements, with applications for the characterization of the blood clotting process, the identification of a blood clot, gelation process, tumor, or fibrosis based on the viscoelastic properties.

25 Claims, 13 Drawing Sheets

(51) Int. Cl.
  *G01N 33/02* (2006.01)
  *G01N 33/483* (2006.01)
  *G01N 33/487* (2006.01)

(52) U.S. Cl.
  CPC ....... *G01N 33/4833* (2013.01); *G01N 33/487*
    (2013.01); *G01N 2291/022* (2013.01); *G01N*
    *2291/023* (2013.01); *G01N 2291/106*
    (2013.01)

(56) References Cited

U.S. PATENT DOCUMENTS

| | | |
|---|---|---|
| 6,951,544 B2 | 10/2005 | Trahey et al. |
| 9,031,701 B2 | 5/2015 | Mola et al. |
| 9,272,280 B2 | 3/2016 | Mola et al. |
| 9,494,475 B2 | 11/2016 | Hadj Henni et al. |
| 9,585,631 B2 | 3/2017 | Vappou et al. |
| 9,726,647 B2 | 8/2017 | Walker et al. |
| 2010/0016718 A1 | 1/2010 | Fan et al. |
| 2010/0069751 A1 | 3/2010 | Hazard et al. |
| 2010/0125199 A1 | 5/2010 | Joo et al. |
| 2016/0274015 A1 | 9/2016 | Hadj Henni et al. |
| 2017/0367683 A1* | 12/2017 | Zheng ................... G01S 7/6263 |

OTHER PUBLICATIONS

Ferrante et al., A Novel Device for the Evaluation of Hemostatic Function in Critical Care Settings, Anesth. Analg., 123(6):1372-79 (2016).

Hobson et al., Resonant acoustic rheometry for non-contact characterization of viscoelastic biomaterials, Biomat., 269:120676 (2021).

Krebs et al., A portable blood plasma clot micro-elastometry device based on resonant acoustic spectroscopy, Rev. Sci. Instrum., 86(7):075005 (2015).

Li et al., Resonant Acoustic Rheometry to Measure Coagulation Kinetics in Hemophilia A and Healthy Plasma: A Novel Viscoelastic Method, Semin. Thromb. Hemost., 49(02): 201-208 (2023).

Nightingale, Acoustic Radiation Force Impulse (ARFI) Imaging: a Review, Curr. Med. Imaging Rev., 7(4):328-339 (2012).

Oyen, Mechanical characterization of hydrogel materials, Int. Mater. Rev., 59(1):44-59 (2014).

\* cited by examiner

A

B

RESONANT ACOUSTIC RHEOMETRY FOR CHARACTERIZATION OF SOFT VISCOELASTIC MATERIALS

GOVERNMENT LICENSE RIGHTS

This invention was made with government support under DE026630 awarded by the National Institutes of Health (NIH). The government has certain rights in the invention.

FIELD OF THE INVENTION

The disclosure relates generally to methods for measuring viscoelastic properties of materials longitudinally in contactless fashion, and more particularly for utilizing ultrasound for generating and tracking surface or interfacial oscillations of biomaterials.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

The mechanical characterization of biological fluids, tissues, and other soft biomaterials is important for basic scientific research, engineering applications, and clinical diagnostics. Compared to the testing of metals or stiff materials, mechanical quantification of soft viscoelastic biomaterials can be particularly challenging due to their relatively low elastic modulus, time-dependent mechanical response, and biphasic structure. Conventional material testing approaches used for soft biomaterials often include tension, compression, indentation, and shear-based methods that are contact based. These techniques are generally unable to track temporal changes in material properties due to the potential for sample contamination and damage resulting from direct contact with a material as well as the slow speed of measurements. This is problematic, as the properties of biomaterials are not always static and can undergo significant viscoelastic changes over a variety of time scales. The relevance of quantitative assessment of soft materials has been recognized in a wide range of fields including tissue engineering, regenerative medicine, bioprinting, as well as food sciences.

An important clinical application of viscoelastic material testing is in the measurement of blood coagulation, which may be useful as an indicator of pathologies ranging from coronary artery disease to diabetes and may further be a useful metric to track heparin treatment following major cardiovascular surgeries. There are a few approaches currently available that accurately measure changes in blood clot viscoelastic properties. For example, viscoelastic hemostatic assays, such as thromboelastography (TEG) or rotation thromboelastometry (ROTEM), can obtain real-time measurements of clot strength. However, these contact-based techniques are both limited by a low sample throughput and relatively high sample blood volume requirements.

Given the high prevalence/incidence of coagulopathic diseases, a device that can improve the throughput and decrease the cost of viscoelastic hemostatic assays would be highly desirable within hospitals, primary care centers, and across the medical field.

A variety of non-contact testing modalities have been exploited using optical, acoustic, or magnetic forces. Ultrasound approaches offer an advantageous strategy for mechanical measurement. Ultrasound is widely used as a non-destructive, non-ionizing modality in medical imaging. Ultrasonic pulses can penetrate and propagate in both solid and liquid mediums, and the scattering or reflection by local inhomogeneity and variation in acoustic impedance along the line of sight may be used to determine the location and properties of the scatterers. Specifically, backscattered signals, or echoes, of a single pulse can be used to generate a 1D amplitude mode (A-mode) image of a single axial line through a material, with the timing and characteristics of individual reflections corresponding to the axial positioning of features within the material.

Ultrasound elastography is an ultrasound imaging modality that detects spatial variation in tissue stiffness based on the difference in internal deformation upon externally applied mechanical compression. These deformations or strains are determined from the temporal shifts of backscattered signals, which correspond to the locations of internal targets before and after the applied compression.

For example, strain elastography provides an external palpitation to a tissue or region under examination and then measures strain of the tissue with an ultrasound transducer. A 2D strain map can be generated for the tissues, allowing for the qualitative measurement of spatial stiffness heterogeneity, where higher local strains indicate a region of lower stiffness and vice versa. While this approach can detect stiffness heterogeneity in a tissue, it generally cannot provide absolute quantitative measures of the intrinsic properties of a material because the stress field cannot generally be predicted in a complex spatial environment. A modification of this technique, Acoustic radiation force impulse (ARFI) imaging, utilizes acoustic radiation force (ARF) to generate tissue deformation in place of external palpation.

In another example, shear-wave elastography imaging (SWEI) utilizes a high intensity ultrasonic pulse to generate acoustic radiation forces within a tissue that result in the generation of shear waves that propagate laterally within the tissues. Lower intensity pulses may then be used to detect the propagation of shear waves, and a shear velocity of the waves may be used to calculate the elasticity of the tissue.

While such ultrasound elastography modalities may provide a convenient method for viscoelastic characterization in vivo, they are not well suited for the characterization of small biomaterial samples in vitro. Further, each technique has limitations in spatial and temporal resolution as well as the types of materials that may be analyzed. Thus, there is a need for techniques capable of measuring elastic and stiffness properties of a broad range of materials with high throughput and temporal resolution.

SUMMARY OF THE INVENTION

The present application describes various techniques and systems for overcoming the limitations of conventional techniques. In particular, rather than measuring deformations within the bulk of a material to estimate elasticity as in ultrasound elastography, in various implementations the present techniques utilize free resonant surface oscillations of a material following an initial, localized surface deformation that is generated by a focused ultrasound pulse. In particular, the resonant surface oscillations allow for measuring surface waves of materials, thereby providing a substantial improvement in sensitivity and measured material properties over conventional techniques that deploy shear wave measurement. The present techniques are substantial improvements over techniques such as sonic Estimation of Elasticity via Resonance (SEER), which utilizes resonant shear waves within the bulk of a material to measure evolving viscoelastic properties during blood coagulation. In SEER, blood samples are added to a proprietary cartridge system that warms the blood, mixes the blood with reagents to induce or alter coagulation, and moves the blood to a conic test chamber where an ultrasound pulse is applied to generate resonant oscillation of the whole sample volume via the acoustic radiation force impulse (ARF). Although the force application in SEER utilizes the ARF of an ultrasound pulse, shear wave propagation within the bulk material is driven by elastic forces, limiting such techniques to measurements of solid blood clots, and thereby missing any potential viscoelastic changes that may be occurring while the blood is still in a liquid state. Additionally, ultrasonic tracking of shear waves requires acoustic scattering elements within the samples (like blood cells) and is unable to generate measurements in materials without detectable acoustic scatters, such as hydrogels or other materials made of constituents or with low concentrations of scatterers.

The present techniques provide substantial improvements over other resonant techniques, include viscoelastic testing of bilayered materials (VeTBiM), which does measure resonant surface waves using entirely different techniques that are not ultrasound-based for both generating and detecting these waves. Further, VeTBiM utilizes a custom cylindrical sample holder with a soft elastomeric bottom. Resonant oscillations are generated by external vibration of the entire holder, and the resonant oscillations of the bilayer construct are measured from the bottom using an optical sensor. The technique throughput is severely limited by the requirement of these custom sample holders.

The present application differs from the technique of acoustic droplet ejection (ADE). ADE techniques use an ultrasonic toneburst directed through the bottom of a microwell plate to apply localized force due to the ARF of the ultrasound field at the surface. When the ARF exceeds the surface tension and gravity, a droplet of liquid may be generated. ADE techniques use the ARF of the ultrasound pulse to expel nanoliter and picoliter droplets of liquid from the well. The technique has been used for assessing the surface tension and viscosity of liquids by generating a surface perturbation below the threshold required for droplet ejection. However, this approach has only been applied to liquids, and doesn't acknowledge or indicate in any way the capability to measure the elastic properties of viscoelastic liquids or solids. Additionally, this methodology treats the liquid surface as a membrane, and while this may allow for a simplistic model of resonant surface waves, the methodology does not capture the physical mechanisms of surface waves on liquid, nor does the methodology allow for the inclusion of elastic properties into the model.

The present techniques, by contrast, utilize hydrodynamic models to describe the behavior of capillary and Rayleigh waves that propagate, respectively, on liquid and solid surfaces. By using resonant surface waves in samples with limited surface area, the present techniques overcome the disadvantages of requiring a large surface area to measure propagating surface waves that the hydrodynamic models describe. The present techniques thus allow more accurate calculation of liquid properties, like surface tension and viscosity, as well as allow for the inclusion of elastic parameters from measurements obtained from small sample volumes with small surface area, providing the ability to measure entirely new classes of materials.

Capillary waves are the dominant mode of surface wave for liquids that do not have an elastic component and are driven by surface tension. In liquid-like regimes and low viscosity, the oscillation of a liquid surface can be approximated by the Kelvin frequency, $$\omega_c^2 = \frac{\sigma k^3}{\rho},$$

where k is the wavenumber, $\sigma$ the surface tension, and $\rho$ the density. The damping coefficient, describing the viscous losses during oscillation of a capillary wave, is given by $$\Gamma = \frac{2\eta k^2}{\rho},$$

where $\eta$ is the shear viscosity of the material.

Rayleigh waves are the dominant mode of surface waves propagating on solid hydrogels, where elasticity acts as the restoring force. Here, the dispersion relation relates the surface oscillation, $$\omega_r^2 = \frac{\beta G k^2}{\rho},$$

to the shear modulus, G, where $\rho$ is the material density, k the wavenumber, and $\beta$ a Rayleigh/shear wave proportionality. The damping coefficient of Rayleigh surface waves is determined as $$\Gamma = \frac{0.45\eta k^2}{\rho}.$$

The present application provides techniques for performing an acoustic rheology measurement of a sample material. In particular, the present techniques may include providing, by a first transducer, one or more excitation acoustic pulses, for example, one or a set of a excitation tone bursts. Propagating through both the solid well bottom and the material, using a focused ultrasound transducer, the excitation acoustic pulse induces an initial perturbation at the interface of the material placed at a focal position without requiring any direct physical contact. The interface perturbation is characterized by an initial displacement on the interface followed by free oscillatory motion on the interface forming resonant surface oscillations due to the boundary of sample well. A second transducer provides a set of short acoustic pulses. The second transducer operates in pulse-echo mode, generating short ultrasonic pulses that are spatially confocal and collinear with the excitation focused ultrasound tone burst and detecting the echoes that reflect back from the interface of the material. In various examples, the detection acoustic pulses may be applied before and after the excitation tone burst to detect the surface position before, during, and after the initial surface excitation. In an example, the second transducer detects these echoes from the interface, and generates an electrical signal in response to the reflected echo signals. The second transducer provides these signals to a processor for storage and subsequent determination of displacements at the interface over time. The kinetics of surface oscillation are determined from the displacement as a function of time by the processor, and in combination with hydrodynamic models of surface wave propagation, used by the process, the processor calculates physical properties of the material, including surface energy, shear modulus, and shear viscosity.

In these ways, the present techniques include techniques for performing contactless, non-invasive acoustic rheology measurements on soft biomaterials and other samples. The techniques are able to be used for measuring properties of a wide variety of sample materials, and take only a fraction of a second to perform a single measurement, with the capability to repeatedly apply the techniques with high temporal resolution to capture the changes in material mechanical properties of the same sample longitudinally over a wide range of time scales from minutes, hours, or days. A number of key aspects demonstrate the novelty of the techniques herein where one or more of these aspects are unique in comparison to any from prior methodologies, including the use of acoustics for generation and detections of surface oscillations, the utilization of resonant waves for material characterization, the focus on surface waves in particular, the estimation of material elasticity, and the capability to track dynamic changes in material viscoelasticity at a variety of time scales.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

The present application provides techniques for performing viscoelastic measurements of both solid and liquid materials. In particular, the technique utilizes ultrasound to both generate and track surface displacements of materials to determine the elasticity, viscosity, and/or surface energy of a material. While the described methods may be implemented in a variety of medical and research applications, it should be appreciated that the disclosed technologies may be applied in any other fields for measuring viscoelasticity, stiffness, surface oscillations, surface displacement, or other acoustic or mechanical properties of materials in any field.

The disclosed systems and methods provide a means for characterizing soft biomaterial stiffness by acoustically generating and quantifying resonant oscillations. The base system includes a transducer that generates ultrasonic pulses, a transducer that detects resulting oscillations, and the processing system for calculating the viscoelastic properties of the biomaterial. This system and method enable the ability to rapidly and precisely quantify the viscoelasticity of the sample material both at a single time-point and as it changes over time. The disclosed technologies are effective at performing measurements of a wide range of soft biomaterial with broad ranges of elasticities and stiffnesses. The system has a simplified design as compared to other elastography technologies, and coupled with sophisticated measurement methods, the disclosed system may enable cost- and time-savings in research, industry, and medical diagnostics.

The described systems and methods include the generation and tracking of resonant surface waves in liquids and soft materials. As used herein, "soft materials" may be a liquid, a solid, or any material substance that exhibits surface vibrations in response to an acoustic radiation force impulse (ARF) perturbation. Also described are analytical methods to extract relevant viscoelastic material properties from the resonant oscillatory behavior of a material. The described approach is non-invasive, non-contact, and non-destructive, allowing for dynamic tracking of material properties at a variety of time scales (e.g., on the order of a second, or fractions of a second), which is not offered by other elastography methods. By being non-contact, the disclosed method reduces contamination or damage of materials, tissues, or samples and enables longitudinal tracking and quality control. Further, the described system does not require specialized labware, which makes the system more flexible to be combined with a wide variety of laboratory workflows.

Figure 1:
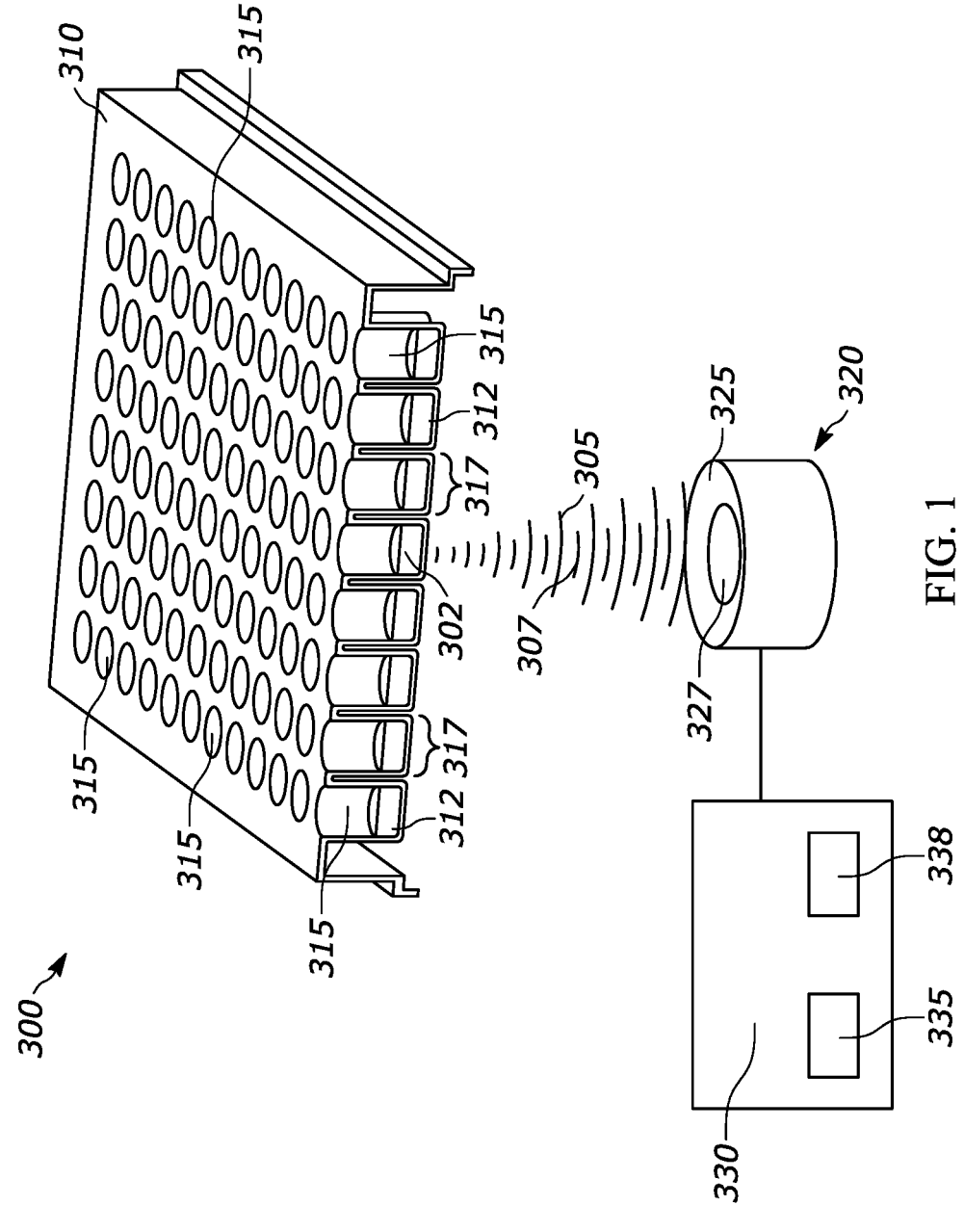
FIG. 1 illustrates a schematic of an example system for characterizing viscoelastic materials using resonant acoustic rheometry using dual transducers aligned underneath a well microplate, in accordance with an example.

FIG. 1 illustrates an example resonant acoustic rheometry (RAR) system 300 for implementing the methods and processes described and illustrated herein. The resonant acoustic rheometry system 300 includes a well plate 310 having wells 315 and a transducer device 320 physically positioned and configured to provide acoustic energy to the wells 315. The wells 315 contain a sample 302. Additionally, each well 315 has a well width 317 with each well 315 supporting resonance vibrations having wavelengths determined by the sample 302 and the well width 317. The well 315 may further be referred to as a "chamber" herein as the well 315 may have various geometries for containing the sample 302. The sample 302 may include a hydrogel, blood, fluid, or solid for performing measurements as provided in the methods and processes described herein. The sample 302 may include one or more proteins, polysaccharides, or other materials. The disclosed methods may be performed on samples 302 of less than 100 μL of material, between 100 and 500 μL of material, between 500 μL and 1 mL of material, or between 1 mL and 10 mL of material. Further, the described methods may be useful for performing measurements and analysis of any interface of two surfaces such as an interface of the sample 302 with air, or the sample 302 with another fluid, or any other fluid-fluid or fluid-solid interfaces.

A first transducer 325 provides an external force in the form of acoustic pulses 305 to the sample 302. In various examples, the acoustic pulse 305 is a tone burst, i.e., a sinusoidal burst with a high pressure amplitude and duration relative to the second acoustic pulses 307. The sample 302 has a surface 312a at the focus of the applied acoustic pulses 305. The sample 302 undergoes a deformation of the surface 312a in the direction of the ultrasonic waves and generates surface waves on the sample 302 that propagate laterally along the surface of the sample 302. The shear waves reflect off of interior surfaces of the well 315 resulting in resonant standing waves being supported by the well 315 and the sample 302. The standing waves further cause the surface 312a of the sample 302 to oscillate at the frequency of the standing wave. This surface 312a, which is an interface of the sample in the illustrated example, may be coated, for example, using surface coatings to alter the contact angle of liquid samples in the well to minimize meniscus formation and to compensate for samples with variable surface tension. Example surface coatings include plasma treatment (tissue culture treatment), silanization, siliconization, fluorosiliconization, pegylation, and petrolatum coating. For solid materials, surface roughness at the interface may be altered, for example, through etching to increase roughness or polishing or coating to reduce roughness.

A second transducer 327 provides confocal and coaxial ultrasonic pulses 307 in a pulse-echo mode to track the motion of the surface 312a. The second acoustic pulses 307 reflect off of the oscillating surface 312a of the sample 302 generating echoes 337 indicative of the motion of the surface 312a. The second transducer 327 generates an electrical signal indicative of the detected pulses. The electrical signal may then be provided to a processor 330 for processing the signal and determining a displacement of the surface 312a over time, i.e., displacement of the interface as a function of time. The displacement at the surface 312a of the sample 202 may include determining parameters of an oscillatory response of the sample 302, including, without limitation, a natural frequency, maximum strain, and/or damping coefficient of the sample 302. Each of the parameters of the oscillatory response may depend on a size and shape of the sample 302 and a material composition of the sample 302. Further analysis of the oscillatory response of the sample 302 may be used to determine viscoelastic properties and other material properties as further described in reference to the method and system described herein.

As illustrated in the cutaway drawing, in an example, the well plate 310 has 96 individual wells 315 each with an equal, or substantially equal, well width 317. In other examples, the well plate 310 may have 1 well, 5 wells, 50 wells 100 wells, or another number of wells. Additionally, the wells 315 may have varying well widths 317, and/or well shapes. For example, the wells 317 may be a hollow cylinder (as illustrated in FIG. 1), a cube, rectangular cuboid, pyramid, or another hollow polyhedron for positioning a sample inside of. The wells 317 may have sidewalls that are parallel, or sidewalls that are not parallel such that a distance between sidewalls, or a diameter, of the well changes along the depth of the well. That is, the inner walls of the wells may be vertical (90° relative to bottom), taper out (>90° relative to bottom), taper in (<90° relative to bottom), or have another configuration. Further, one or more of the wells 317 may be tunable in shape and/or size. For example, a bottom wall of one or more of the wells may be tunable to provide more or less volume inside of the well 317, and outer walls of the well 317 may be shifted to provide different well shapes (e.g., rectangular to square, circular to elliptical, etc.). Further, the well may have a tunable height (Z-axis), width (X-axis), depth (Y-axis), or diameter for tuning supported resonances of standing waves inside of the well 317. For example, the diameter of the well may be different at base of well, at the sample interface, and/or at the top of well. In some examples, the material surface of the well is consistent throughout. In some examples, the material surface of the well may change. Example material surfaces include polystyrene, polypropylene, glass, acrylic (PMMA), or silicone (PDMS).

The transducer device 320 has a dual transducer configuration having the first transducer 325 and the second transducer 327. The first and second transducers 325 and 327 may both be part of the single transducer device 320, as shown, while in other examples, the transducers 325 and 327 may be independent transducers that are positioned independently relative to the well plate 310 to provide acoustic energy to the wells 315.

The system 300 in the exemplary embodiment of FIG. 1 is constructed with the well plate 310 having 96 wells 315. The transducer device 320 is a circular two-element transducer with the first transducer 325 positioned around an outer radius of the transducer device 320, and the second transducer 327 positioned at a central portion of the circular transducer device 320. Both the first transducer 325 and the second transducer 327 have a spherical focus, with the transducer device 320 aligned such that the foci of both the transducers 325 and 327 are at a position at about the center of the solution surface 312a to induce a force at the air-solution surface interface. The transducer device 320 is physically coupled to a 3D motion platform as the motion actuator 332 that allows for automated control of the position of the transducer device 320. Therefore, in the exemplary embodiment of FIG. 1, the transducer device 320 can be moved and aligned to provide excitation pulses 305 to any surface 312a of the sample 302 in any of the wells 315.

The transducer device 320 may be physically coupled to a translation stage 332 that controls a position of the transducer device 320. The translation stage 332 may be a three-dimensional (3D) translation stage that can move the transducer in an X, Y, and Z axis direction to position the transducer device 320 relative to the well plate 310 to provide the pushing and tracking pulses 305 and 307 to a well 314 of the well plate 310. In examples, the transducer device 320 may have a focal position for the acoustic pulses of between 0.5 and 2 inches from a center of the transducer device (i.e., each of the first and second transducers 325 and 327 have a focal point between 0.5 and 2 inches). In examples, the transducer device 320, and transducers thereof, may have focal points of between 0.1 inches and 1 inch, 1 and 2 inches, 2 and 5 inches, 5 and 10 inches, or between 1 and 12 inches. While described as a 3D translation stage, the translation stage 332 may include or more of a single axis translation stage, two-axis translation stage, an actuator, a motor, or another element for controlling the position of the transducer device 320 relative to the well plate 310. Further, in examples, the transducer device 320 may be stationary and the position of the well plate 310 may be controlled and moved to position the wells 315 relative to the transducer device 320 for performing the methods described herein.

The transducer device 320 is communicatively coupled to one or more processors 330 for performing the methods described herein. The processor 330 may include a controller 335 for controlling the transducer device 320 and/or the translation stage 332, and a memory 338 for storing machine readable instructions 338 that when executed cause the system 300 to perform the methods described herein. In some examples, the processor 330 may be a processing device and may further include one or more input/output devices (e.g., a keyboard, mouse, touchscreen display, etc.), communications modules (e.g., network communications, wifi, Bluetooth, etc.), and other elements for performing the methods herein.

Figure 2A:
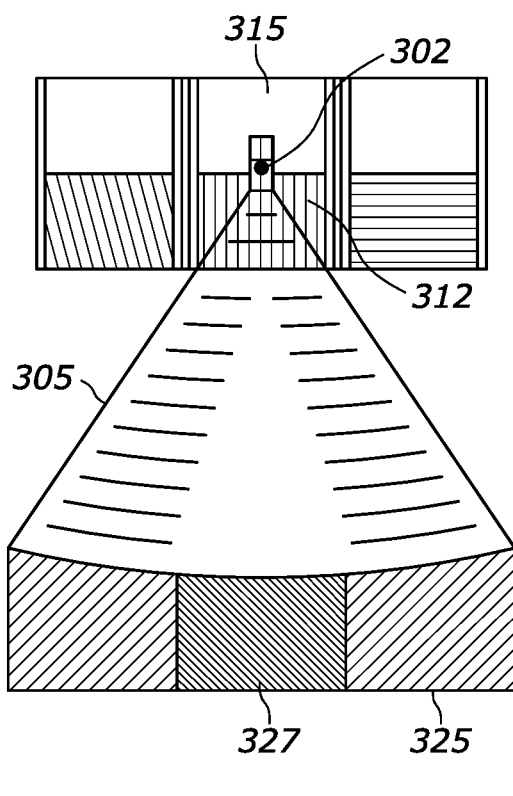
FIG. 2A is a side view of a well from FIG. 1 illustrating one of the dual transducers providing tone burst pulses to the well, in accordance with an example.
Figure 2B:
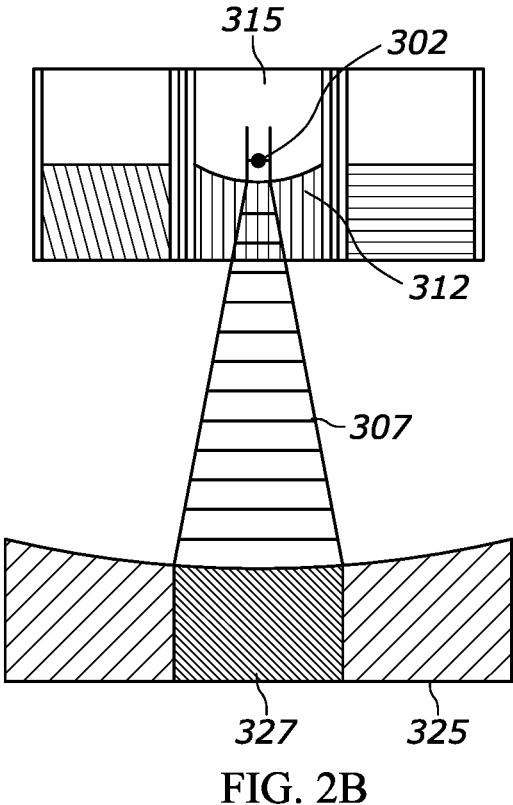
FIG. 2B is a side view of a well from FIG. 1 illustrating the second transducer providing acoustic pulses to the well while in a pulse echo mode, in accordance with an example.
Figure 3:
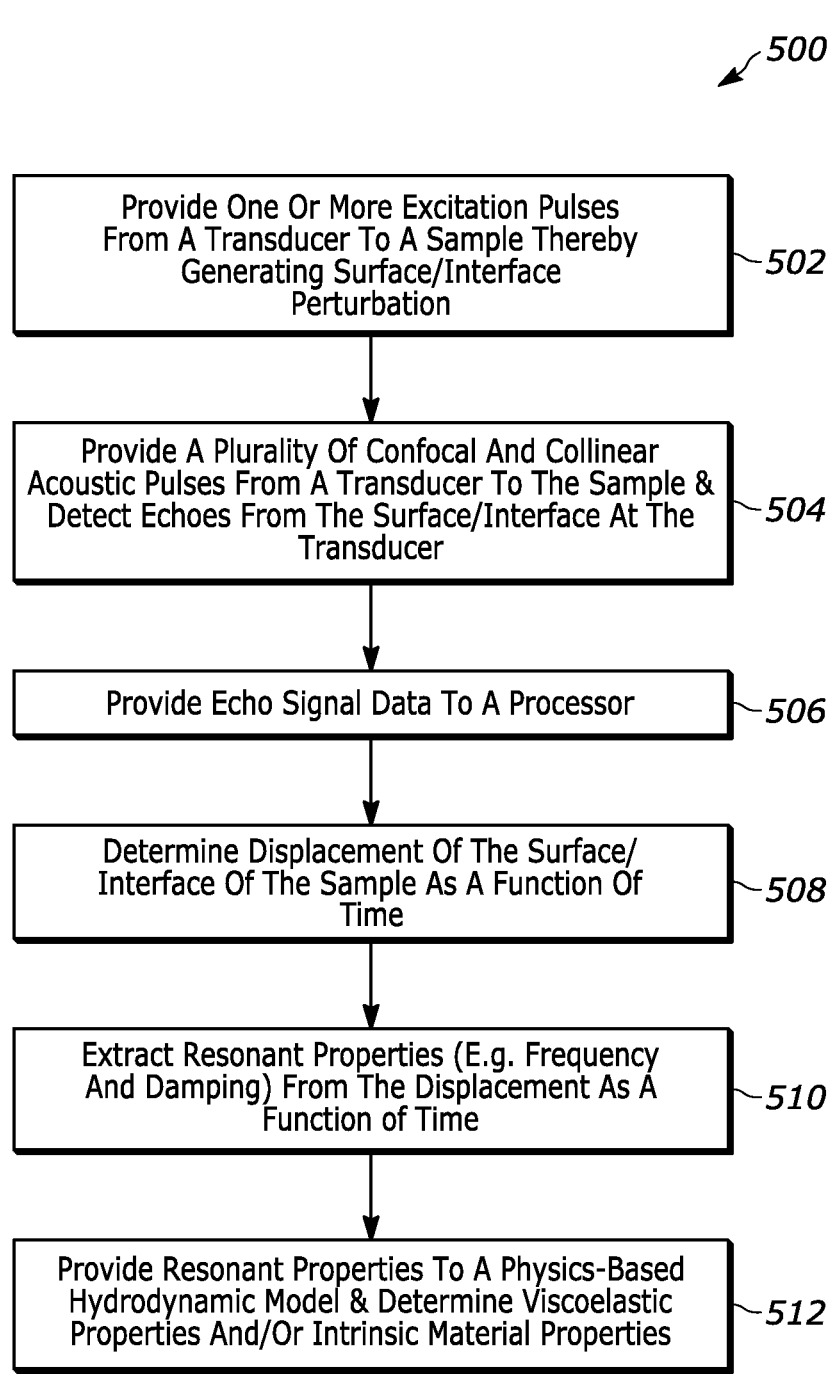
FIG. 3 is a flow diagram of a method for performing or characterizing viscoelastic materials using resonant acoustic rheometry on a sample material, in accordance with an example.

FIGS. 2A and 2B are side views of wells 315 respectively illustrating the transducer providing excitation pulses 305 and tracking pulses 307. FIG. 3 is a flow diagram of a method 500 for performing resonant acoustic rheometry on a sample. The method 500 may be performed by the system 300 of FIG. 1. For clarity, the method 500 will now be described with reference to FIGS. 3, 2A and 2B.

Initially, the transducer device 320 is positioned to provide acoustic energy in the form of two different types of pulses to the sample 302 disposed in the well 315 of the well plate 310. The first transducer 325 provides one or more excitation pulse 305 (which may be excitation tone bursts) to sample, in particular at a focal point to the well 315, containing the sample 302 (block 502), as shown in FIG. 2A. In response, the sample 302 deforms according to the applied acoustic energy in the form of the excitation pulses 305. The deformation of the sample 302 causes transverse waves on the surface 312a that reflect off walls of the well 315 forming standing waves in the well 315, as previously described. The standing waves cause oscillations of the surface 312a of the sample 302. The excitation pulses 305 may be acoustic waves having a frequency of less than 1 MHz, of between 1 and 5 MHz, of between 5 and 10 MHz, of between 1 and 10 MHz, of between 10 and 25 MHz.

The second transducer element 327 of the transducer device 320 provides, to the sample 302, the tracking pulses 307 as a second set of acoustic pulses (block 504). At least a portion of the tracking pulses 307 reflect off of the oscillating surface of the sample resulting in reflected echoes 337. The second transducer element 327 detects the echo pulses and generates an electrical signal indicative of the detected echo pulses 337 (block 506). The tracking pulses may be acoustic waves having a frequency of between 1 and 5 MHz, of between 5 and 10 MHz, of between 1 and 10 MHz, of between 1 and 20 MHz, of between 10 and 25 MHz, etc.

The second transducer element 327 provides the electrical signal indicative of the detected echo pulses to the processor 330 (block 506). The processor 330 then performs signal analysis of the electrical signal indicative of the detected echo pulses and determines characteristics of the echo pulses.

In an implementation of the method 500, the processor 330 determines, based on the signal indicative of the echoes 337, a displacement as a function of time of an interface of the sample 302 over time (block 508). The interface of the sample 302 may be the surface 312a of the sample 302 at a sample/air interface. More generally, the interface of the sample 302 may be at any surface of the sample 302. The processor 330 determines the displacement of the interface of the sample 302 over a period of time being a sampling period of time that the second transducer 327 provides tracking pulses 302, and receives echo 337 from the sample 302. In some examples, the second transducer 327 may provide tracking pulses 307 at a rate of between 1 and 20 kHz to provide a sampling rate of the displacement of the sample 302 of between 1 and 20 kHz.

In some examples, the processor 330 may determine the time dependent displacement from a plurality of displacements of the interface of the sample 302, with each displacement at a different point in time of the sampling period. The displacement of the interface of the sample 302 may be determined with a spatial resolution along the Z-axis of 1 μm, 2 μm, 5 μm, between 0.5 and 1 μm, between 0.5 and 2 μm, between 1 and 10 μm, etc. The displacement of the interface of the sample may further be determined with an axial resolution, along the X and/or Y axes, of 0.5 μm, 1 μm, 2 μm, 5 μm, between 0.5 and 1 μm, between 0.5 and 2 μm, between 1 and 10 μm, etc. The processor 330 may determine an oscillatory motion of the interface of the sample 302 from the time dependent displacement of the interface. The oscillatory motion may be determined to follow a damped, underdamped, overdamped, harmonic, standing wave, or similar oscillatory model.

The processor 330 may determine, from the displacement as a function of time of the interface of the sample 302, one or more resonant properties of the sample 302 by spectral fitting (block 510). For example, the processor 330 may determine one or more parameters of materials of the sample 302 including a maximum displacement amplitude, natural frequency, and/or damping coefficient. From the determined one or more viscoelastic properties, the process 330 may apply these properties to a physics-based hydrodynamic model and determine intrinsic properties of the sample, such as a shear elasticity, a shear viscosity, and an interface energy (block 512).

The method 500 of FIG. 3 may be performed once to determine the viscoelastic properties of a material over a short sampling period (e.g., seconds, or minutes), or the method 500 may be performed a plurality of times for measuring or monitoring the viscoelastic properties of materials or samples over a longer period of time. Monitoring a sample over longer periods of time allows for the observation of dynamic properties of a material such as changes in elasticity or viscosity, properties which may be useful for performing determining chemical or physical changes to the microstructure of a sample.

To perform analysis of dynamic properties of the sample 302, the excitation transducer 325 may provide repeated excitation pulses 305 to generate oscillations of an interface (e.g., the surface 312a) of the sample 302. The excitation pulse(s) 305 may include a series of sinusoidal tone bursts having a same frequency, or different frequencies to illicit different responses from a material of the sample 302. The second transducer 327 may provide tracking pulses 307 during periods when the excitation pulse 305 is applied, and periods after the excitation pulse(s) 305 have been applied, or periods both before and after excitation pulse(s) 305 have been applied. The second transducer 327 detects echoes in response to any of these conditions.

In some examples, the processor 330 determines a change in the dynamic viscoelastic properties of the material over time. From these changes, the processor may determine one or more of properties such as the kinetics of a gelation, crosslinking of polymer chains, material hydrolysis, and proteolytic degradation. Further, these and other dynamic viscoelastic properties may be useful for determining a response of the sample 302 to externally applied stimuli, such as an applied acoustic energy, electromagnetic energy, heat energy, or other applied energy or force. The processor 330 may determine, from the dynamic viscoelastic properties, a transition of one or more physical properties of the material, including the material phase from liquid to solid or solid to liquid.

The method 500 may be performed a plurality of times to determine phase changes of a material of the sample 302. For example, the processor 330 may determine a spectrogram or dynamic phase diagram of the material of the sample from one or more dynamic viscoelastic properties. The processor 330 may then determine a complex wave mode transition between surface waves of various material phases, e.g. capillary or Rayleigh waves, or between different oscillatory modes of the sample 302 from the spectrogram.

The processor 330 may further determine a position of the well 317 relative to the transducer device 320 from the signal provided by the second transducer 327. For example, the second transducer 327 may provide the tracking pulses 307, detect the echoes 337, and provide the signal indicative of the echoes 337 to the processor 330. The processor 330 may then determine locations of edges or sidewalls of the well 317 from the signal. The controller 335 may then control the translation stage 332 to reposition the transducer device 320 at a position relative to the well 317 that is at a focal distance of the transducer, toward a transverse center (X and Y axis) of the well 317, or another position as determined by the processor 330.

Figures 4A, 4B:
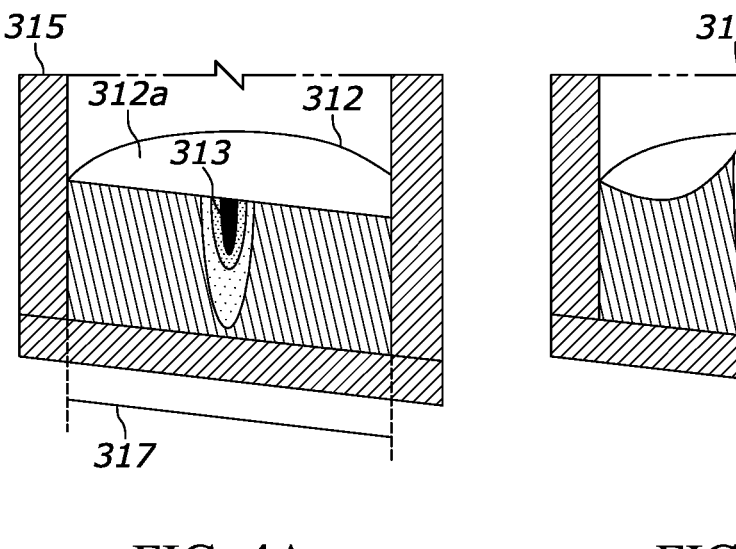
FIG. 4A illustrates a material within a well and an interface having a flat, evenly distributed surface before the application of excitation pulses, in accordance with an example.
FIG. 4B illustrates the material and interface of FIG. 4A after a tone burst has been provided, in accordance with an example.

FIGS. 4A-4D illustrate the concept of the generation of standing waves at a surface 312a of the sample 302 inside of the well 315. The physical phenomena illustrated in FIGS. 4A-4D are indicative of the displacement of surfaces of the sample 302, and the surface 312a of the sample 302 of FIG. 3, due to the application of the excitation pulses 305 at block 502 of the method 500 of FIG. 3. FIG. 4A illustrates the solution surface as a flat, evenly distributed surface before the excitation pulses 305 are provided. The excitation pulses 305, illustrated in FIG. 1, are provided to the surface 312a in FIG. 4A to exert a force 313 on the sample surface 312a. The excitation pulses 305 cause the solution surface 312a to deform in the positive Y direction, shown in FIG. 4B. The solution surface then rebounds in an opposite direction against the direction of the initial applied excitation pulse 305, shown in FIG. 4C. The excitation pulse 305 may include a sinusoidal tone burst of various powers or durations to cause the deformation of the sample surface 312a. Further, excitation pulse 305 is halted before significant displacement of the solution surface 312a occurs.

Figures 4C, 4D:
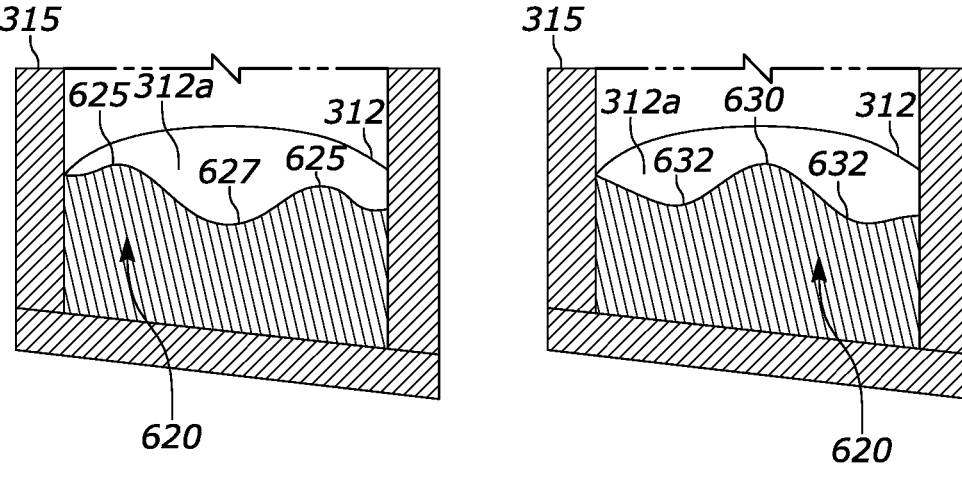
FIG. 4C illustrates a standing wave of the interface of the material of FIGS. 4A and 4B, with an annular peak and a central trough of the standing wave, in accordance with an example.
FIG. 4D illustrates a standing wave of the interface of the material of FIGS. 4A and 4B, with annular troughs and a central peak of the standing wave, in accordance with an example.

FIGS. 4C and 4D illustrate a standing wave 620 of the surface of the sample surface 312a after the application of the excitation pulses 305 has been stopped. FIG. 4C shows the standing wave 620 with annular peaks 625 and a central trough 627. In FIG. 4D, as the solution surface 612a oscillates according to the motion of the standing wave 620, the central trough 627 becomes a central peak 630, and the annular peaks 625 become an annular trough 632. Oscillation of the peaks and troughs of the standing wave 620 repeat in oscillatory fashion, which causes the surface 312a of the sample 302 to oscillate in a similarly resonant oscillatory fashion dependent on the wavelength of the standing wave 620, and the materials and geometries of the sample 302. Characteristics of the oscillations of the surface 312a of the sample 302 (e.g., maximum amplitude, resonant frequency, damping coefficients, etc.) may be useful for determining material properties of the sample, which may further be used for characterization of materials.

Figure 5:
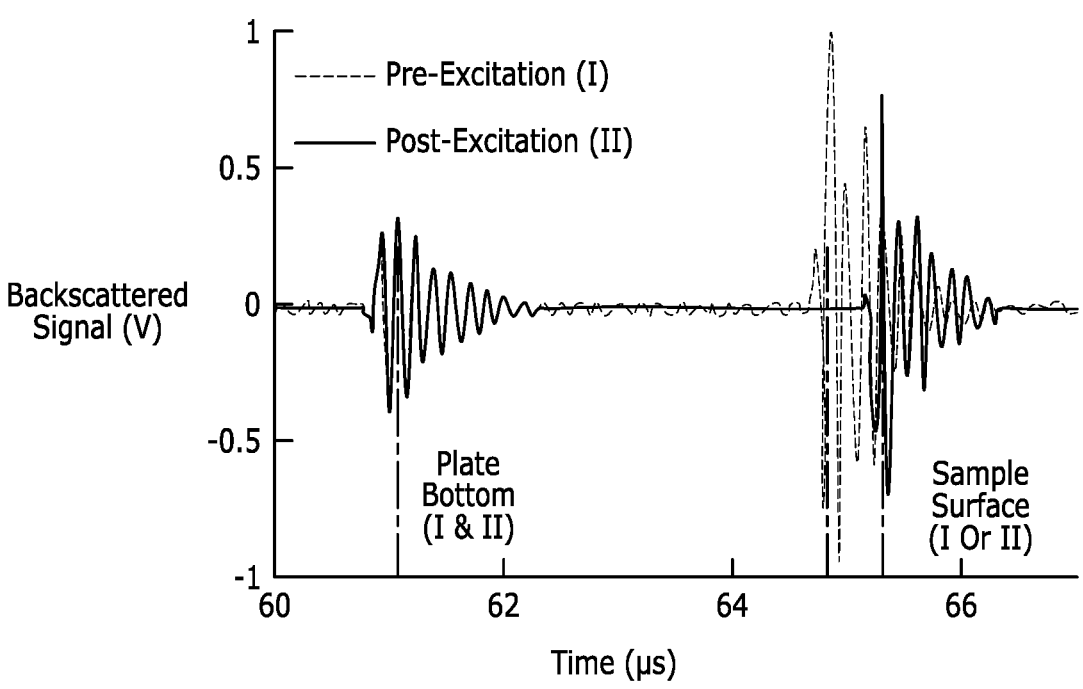
FIG. 5 is a diagram illustrating the application of a tone burst and subsequent pulses to a sample material, in accordance with an example.

FIG. 5 is a diagram illustrating the application of the excitation and tracking pulses 305 and 307 in accordance with the examples and data provided herein. In the exemplary embodiment, the second transducer 327 provides a series of tracking pulses over a sampling period to continuously measure the displacement of the surface 312a of the sample 302. The pushing transducer 325 provides a single tone-burst pulse to generate the standing wave in the well 315. A portion of the energy provided by the tracking pulses 307 is reflected off of the surface 312a of the sample 302 as an echo 337. The echo pulses 337 are then received by the second transducer 327 and further processed and analyzed as described further herein.

Figure 6:
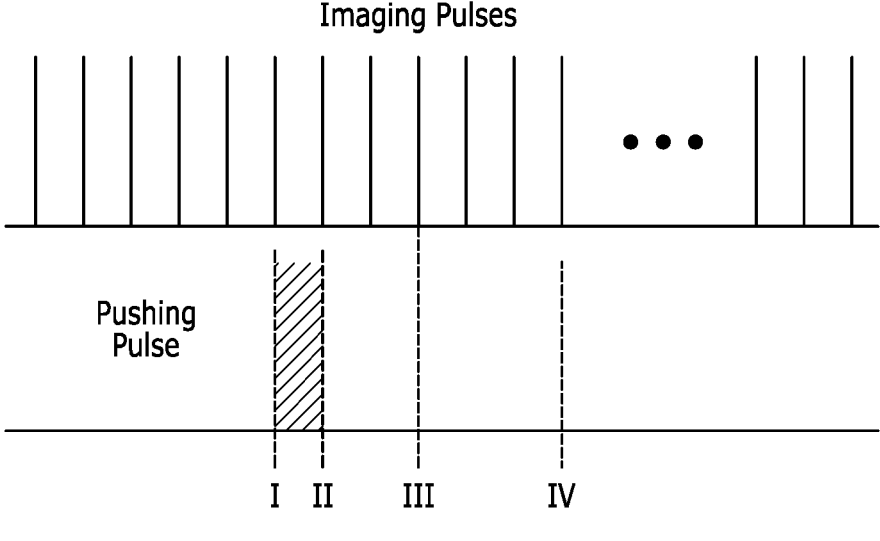
FIG. 6 is a plot of the echoes collected by a second transducer used for estimation of displacement and for determining one or more viscoelastic properties, in accordance with an example.

FIG. 6 is a plot of the acoustic echoes reflected off the surface 312a of the sample 302 due to the application of the tracking pulses 307, with an echo detected before and an echo detected after the application of the excitation pulse 305. The time shift in the collected echoes is used to determine the displacement of the surface 312a of the sample 302 at the time of the tracking pulse 307.

Figure 7:
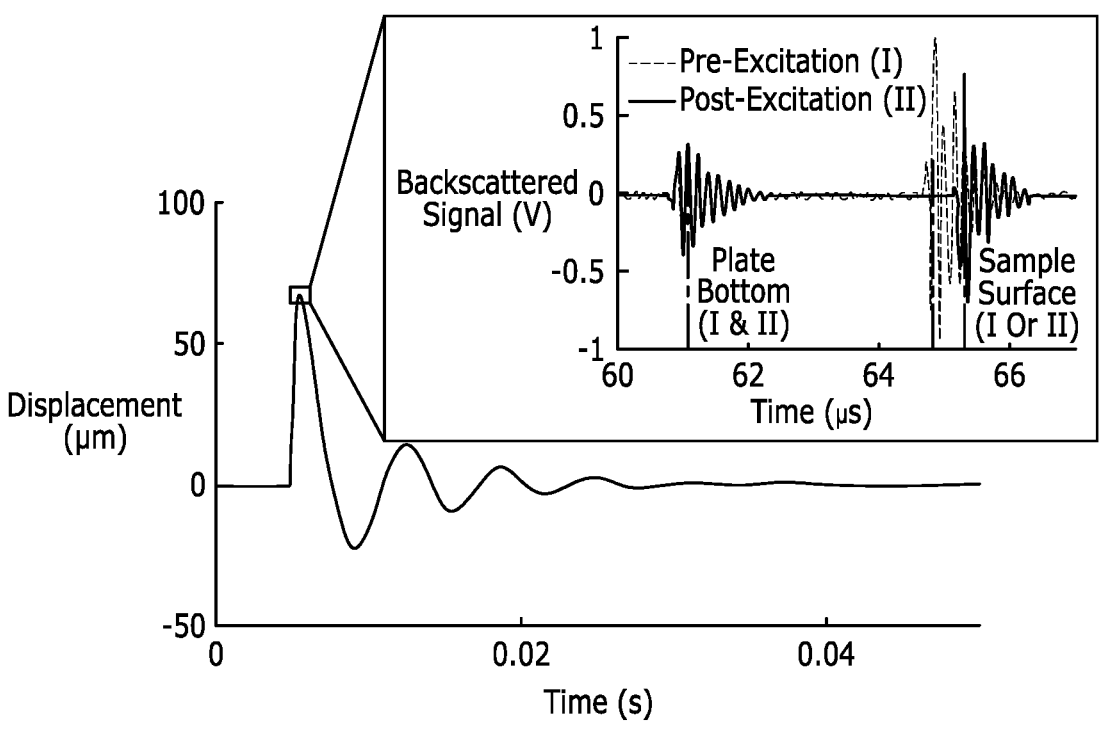
FIG. 7 is a plot of the displacement profile of a material interface over time as measured by the system of FIG. 1, in accordance with an example.

FIG. 7 is a plot of the displacement of the solution surface 312a over time as measured by the system 300 of FIG. 1. The displacement of the solution surface 312a has an initial peak 1010, after which the solution surface 312a exhibits a damped harmonic oscillator profile having a resonant frequency ω, and damping coefficient Γ. The resonant frequency and damping coefficient may be used to further determine viscoelastic properties or characteristics of materials.

Figure 8:
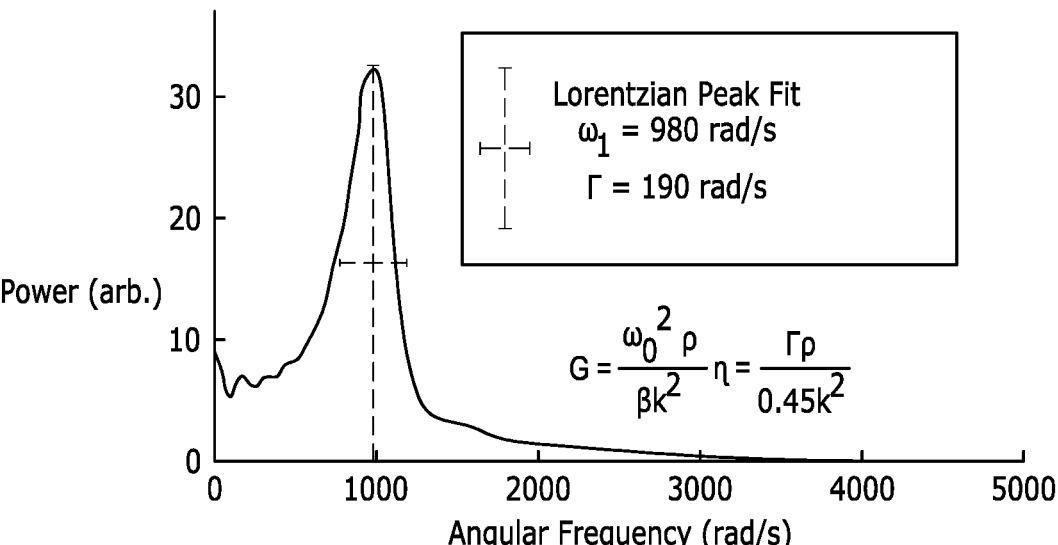
FIG. 8 is a plot of a power spectral density as a function of frequency, which was calculated using a Fourier transform of the time domain data presented in FIG. 7, in accordance with an example.

FIG. 8 is a plot of the power spectrum taken as the Fourier transform of the time domain data presented in FIG. 7. The peak shown in FIG. 8 may be modeled using a Lorentzian peak fit with the frequency position and half-width at half-maximum (HWHM), providing the resonant frequency $\omega_0$ and damping coefficient Γ, respectively. Using hydrodynamic models of Rayleigh wave propagation it is therefore possible to calculate the shear modulus G and viscosity η according to the following equations.

$$G = \frac{\omega_0^2 \rho}{\beta k^2} \quad \eta = \frac{\Gamma \rho}{0.45 k^2}.$$

Figures 9A, 9B, 9C:
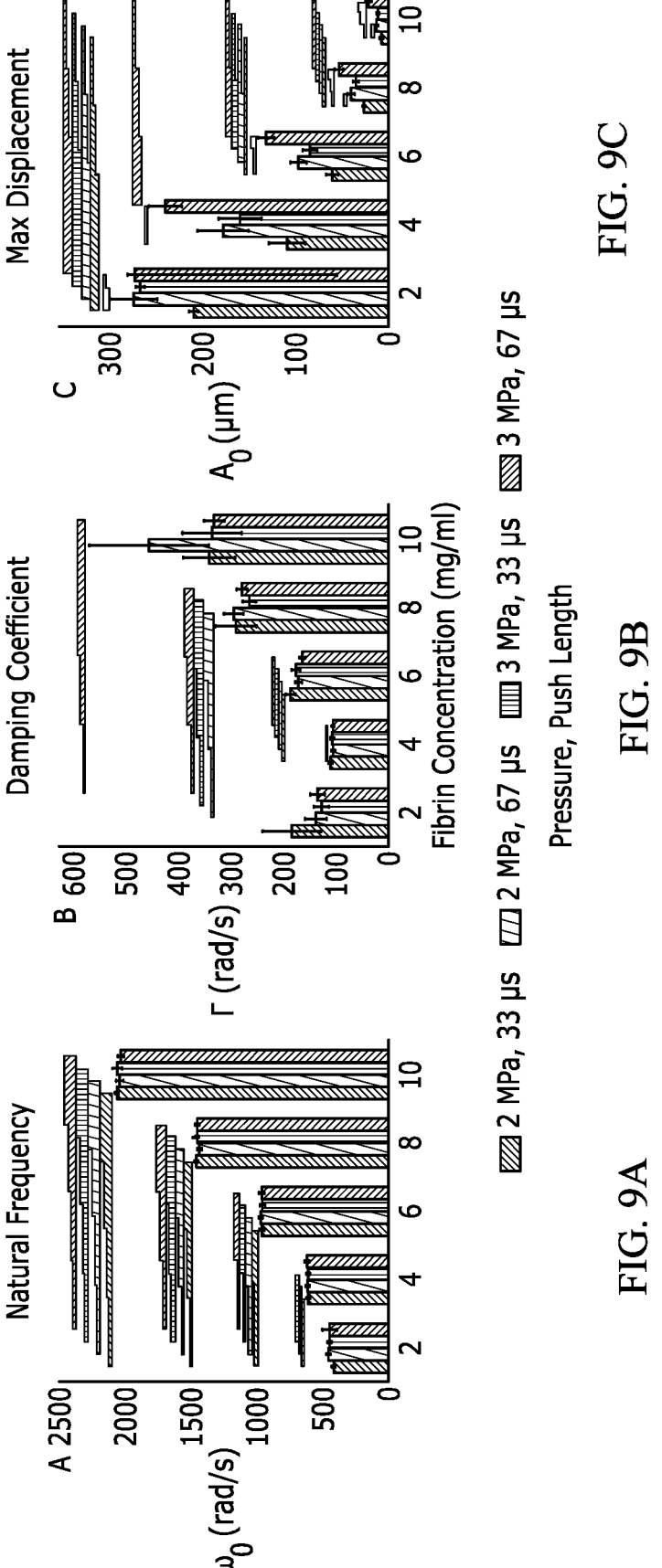
FIG. 9A is a plot of natural frequency of surface oscillations for various concentration fibrin gels with varied intensities and durations of applied excitation pulses, in accordance with an example.
FIG. 9B is a plot of damping coefficient of surface oscillations for various concentration fibrin gels with varied intensities and durations of applied excitation pulses, in accordance with an example.
FIG. 9C is a plot of maximum displacement of surface oscillations for various concentration fibrin gels with varied intensities and durations of applied excitation pulses, in accordance with an example.

FIGS. 9A-9C are plots presenting the natural frequency $\omega_0$, damping coefficient Γ, and maximum displacement of the first surface 302a of the sample 302 with varied intensities and durations of the applied excitation pulses 305 for samples 302 having different fibrin concentrations. In the exemplary embodiment of FIGS. 9A-9C, excitation pulses 305 were provided at 2 or 3 MPa peak pressures for 33 μs or 67 μs intervals. As demonstrated by FIGS. 9A-9C, the resonant frequency of the displacement of the sample 302 is independent of the intensity or duration of the excitation pulse 305, but increases significantly with increasing fibrin concentration. The amplitude of the maximum displacement of the sample 302 varies greatly due to the different forces and durations of the excitation pulse 305. The longer-applied excitation pulses 305 may result in greater maximum displacements. The damping coefficient also exhibits differences due to the applied force and duration, which display dependence on the concentration of fibrin of the sample 302.

Figures 10A, 10B, 10C:
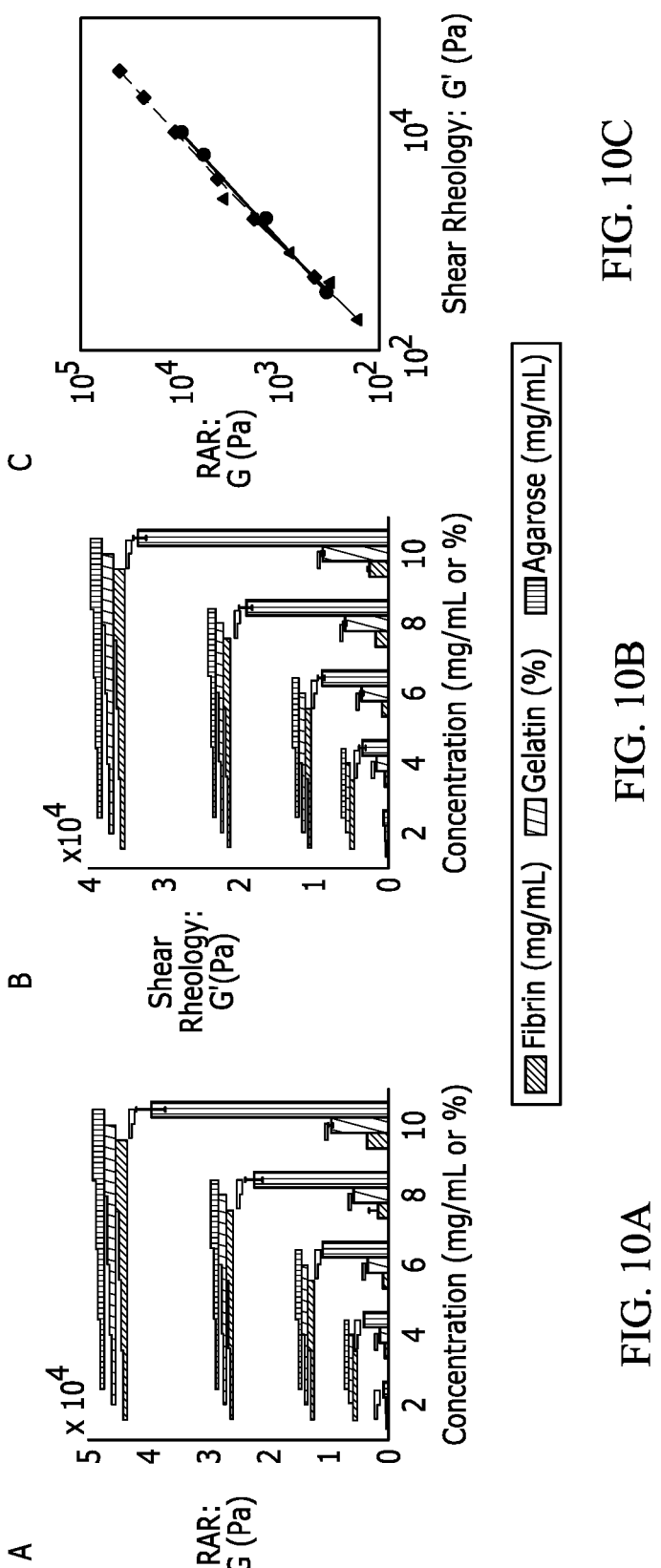
FIG. 10A is a plot presenting resonant acoustic rheometry measurements of the shear modulus for fibrin, gelatin, and agarose samples of varying concentrations, in accordance with an example.
FIG. 10B is a plot of shear rheometry measurement of the shear modulus for fibrin, gelatin, and agarose samples of varying concentrations, in accordance with an example.
FIG. 10C is a plot of resonant acoustic rheometry versus shear rheometry measurements of shear modulus for fibrin, gelatin, and agarose samples of varying concentrations, in accordance with an example.
Figures 10D, 10E, 10F:
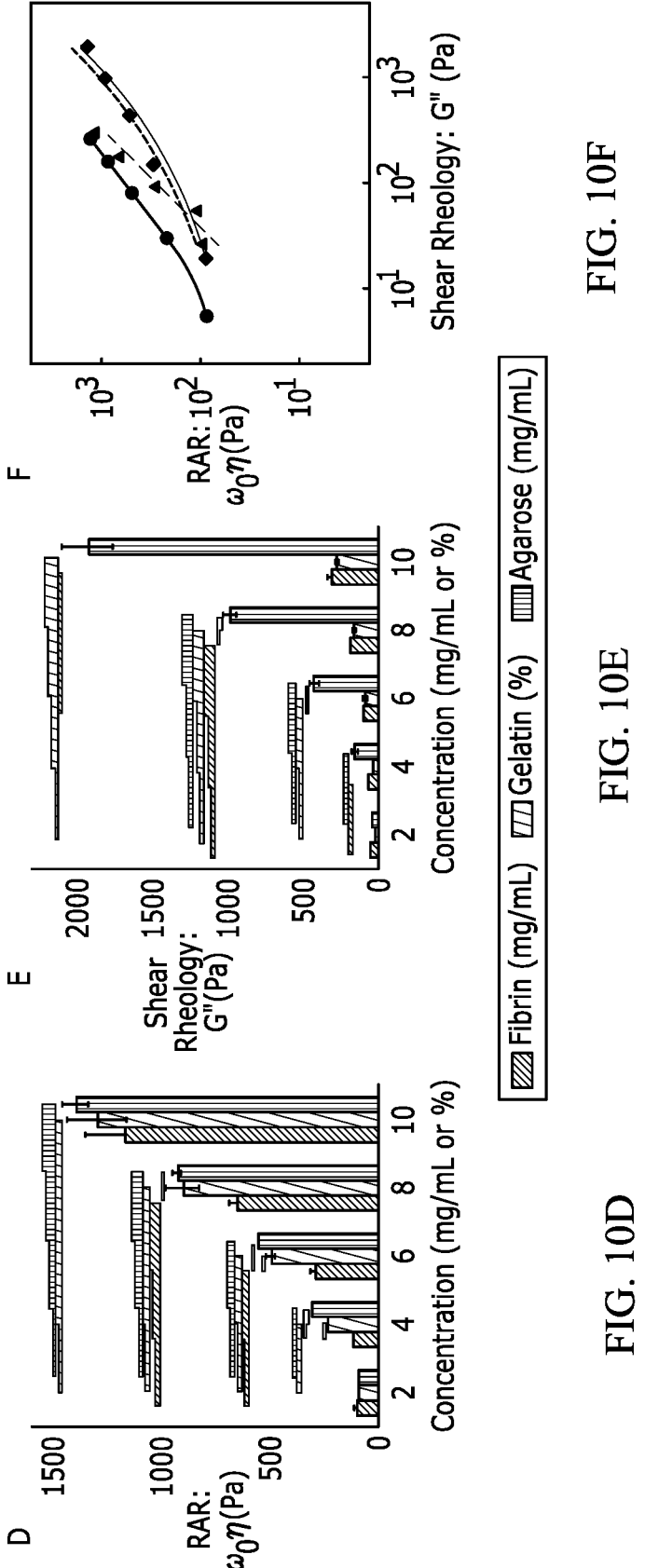
FIG. 10D is a plot of loss modulus $\omega\eta$ measured using resonant acoustic rheometry for fibrin, gelatin, and agarose samples of varying concentrations, in accordance with an example.
FIG. 10E is a plot of loss modulus G" measured using a shear rheometry for fibrin, gelatin, and agarose samples of varying concentrations, in accordance with an example.
FIG. 10F is a plot of resonant acoustic rheometry versus shear rheometry measurements of loss modulus for fibrin, gelatin, and agarose samples of varying concentrations, in accordance with an example

The methods described herein may be performed on hydrogel samples 302 having different polymer concentrations of either fibrin, gelatin, or agarose having shear moduli ranging from 0.1 to 30 kPa, which is representative of a wide range of soft tissues. FIGS. 10A and 10D are plots presenting the resonant acoustic rheometry (RAR) measurements of the shear modulus, G, and the loss modulus, ωη versus concentration of the sample. FIGS. 10B and 10E are plots of the equivalent shear rheometry measurement, G' and G", versus sample concentration. FIGS. 10C and 10F are plots comparing the RAR measurements of the shear modulus to the shear rheometry measurement for the samples of fibrin, gelatin, and agarose. The data of FIGS. 10A and 10B shows that the measured shear modulus varies between hydrogel types and polymer concentrations. FIG. 100 shows the substantially linear correlation between the data of FIGS. 10A and 10B, having an $R^2$ value of 0.95 for individual materials, and all data sets as a whole.

The viscosity measurement data presented in FIG. 10D also shows differences between sample types and concentrations, with a lower correlation to shear rheometry data across all of the data sets resulting in an $R^2$ value of 0.54, as represented by the curves in FIG. 10F. The RAR viscosity data has a higher correlation when taken as a function of the concentration for each material, resulting in an $R^2$ value of 0.95. The difference between the overall correlation values may be due to differing oscillation frequencies with the present techniques and shear rheometry and the non-Newtonian characteristics of hydrogels. The results presented in FIGS. 10A-10F demonstrate that the disclosed methods for performing techniques herein can be used for performing viscoelastic measurements of materials that is comparable to conventional testing approaches, without requiring contact with the sample. Additionally, the materials used for the measurements presented in FIGS. 10A-10F have a wide range of shear moduli, representing a wide range of soft biomaterials, indicating that the acoustic rheometry methods described herein may be applied in industries that require measurements of a broad range of materials.

Figure 11A:
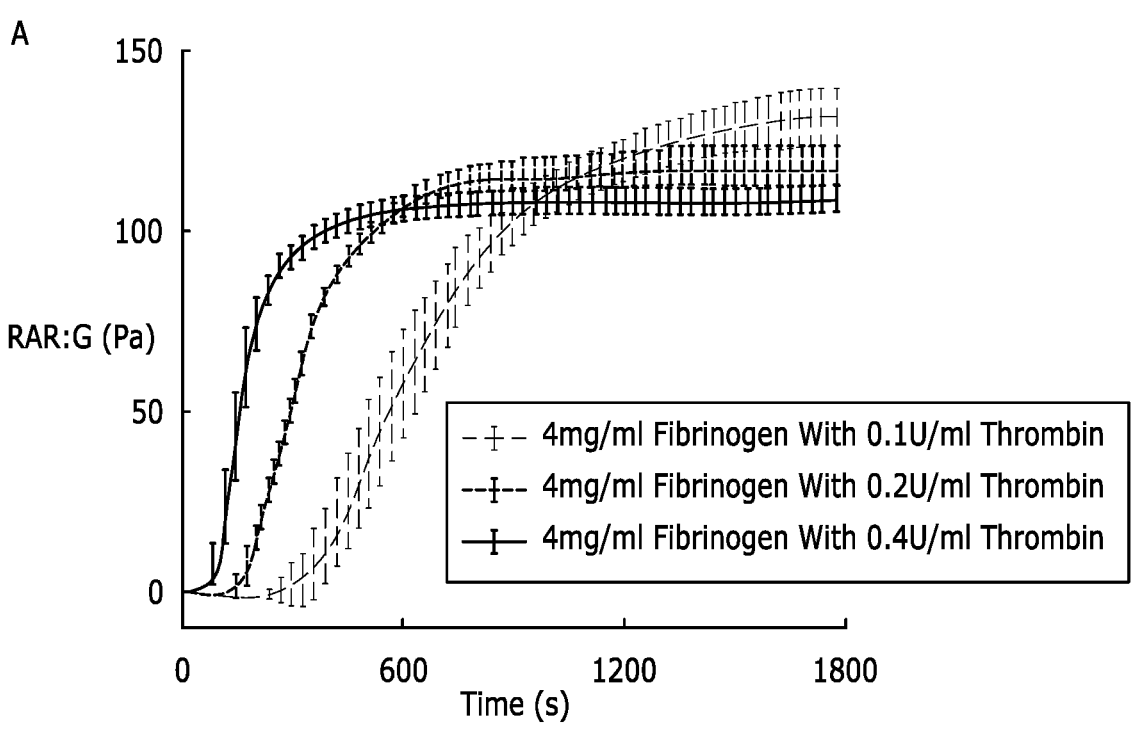
FIG. 11A is a plot of resonant acoustic rheometry measured shear modulus over time during fibrin gelation, in accordance with an example.
Figure 11B:
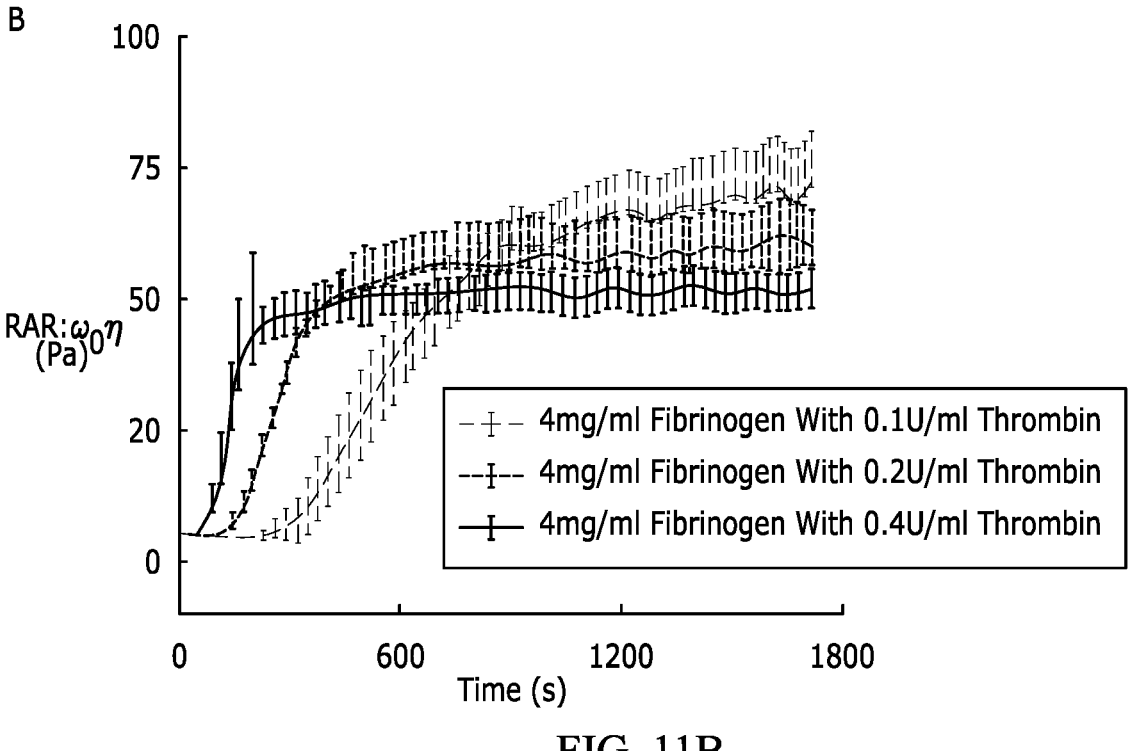
FIG. 11B is a plot of resonant acoustic rheometry measured viscosity over time during fibrin gelation, in accordance with an example.

Dynamic gelation studies were performed using the described methods to track dynamic changes in viscoelastic properties of hydrogels during thrombin mediated fibrin gelation. Repeated measurements were applied to different samples to measure the viscoelastic properties of the samples over a period of time. FIGS. 11A and 11B are plots of the shear modulus and loss modulus measurements of the samples over time. The data presented in FIGS. 11A and 11B shows that the present techniques are capable of measuring dynamic changes in viscoelastic properties and that the rate of gelation and the maximum shear modulus are dependent on the concentration of thrombin.

Figure 12A:
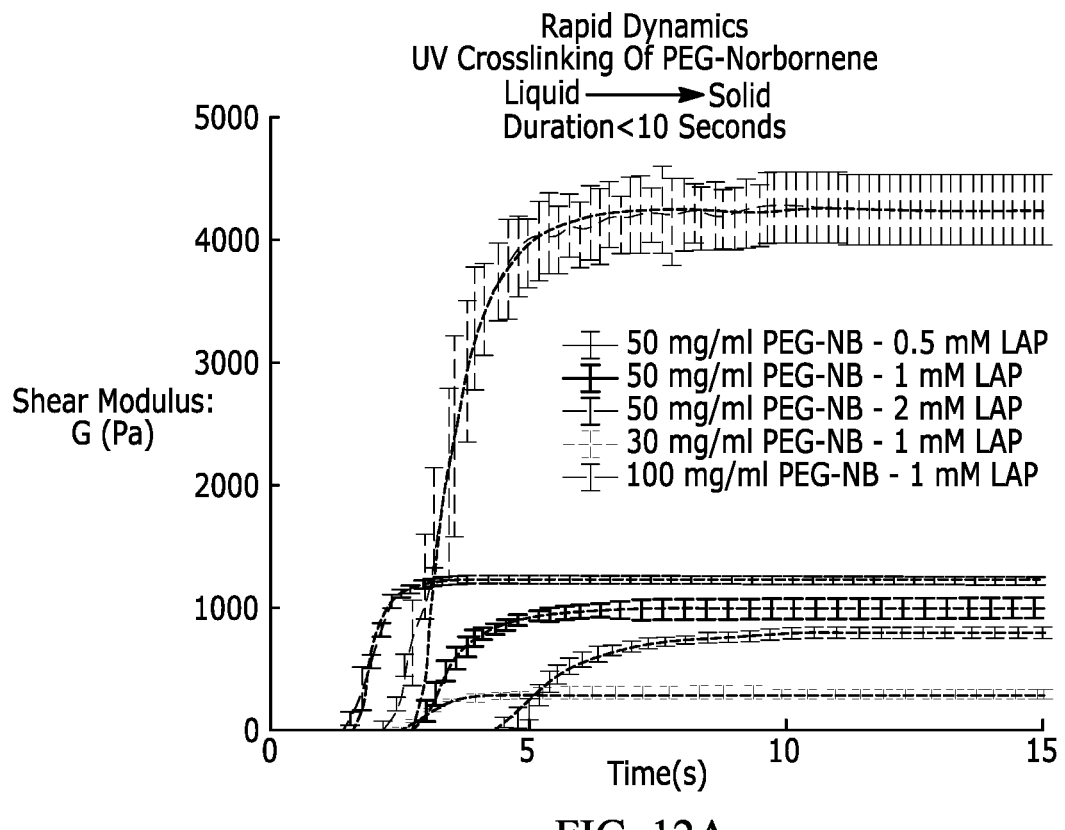
FIG. 12A is a plot of shear modulus versus time for UV crosslinking of PEG-NB, demonstrating a plurality of materials that exhibit rapid dynamic responses, in accordance with an example.
Figure 12B:
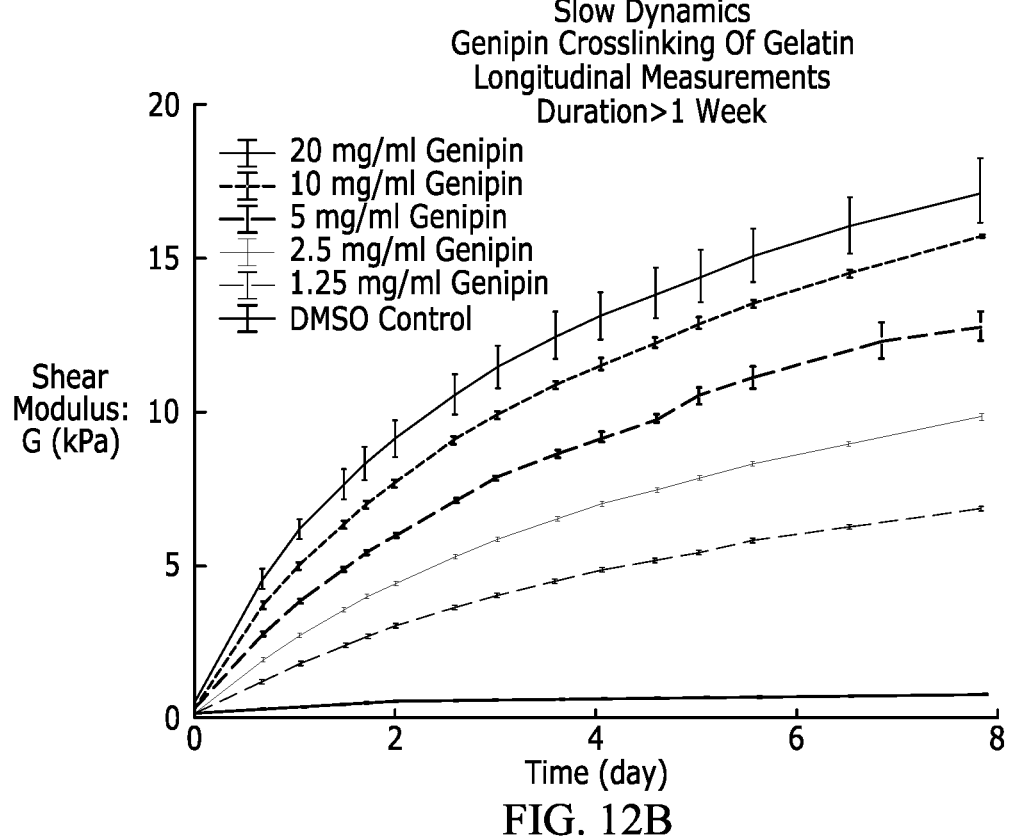
FIG. 12B is a plot of shear modulus versus time for gelatin crosslinking with genipin, representing a plurality of materials that exhibit slow dynamic responses, in accordance with an example.

The disclosed methods were used to measure viscoelastic properties and gelation of a plurality of materials including fibrin, PEG, LAL assays, and whole blood as the samples. Using the present techniques to measure dynamic viscoelastic properties of materials allows for the ability for the present techniques to identify phase transitions in materials. FIGS. 12A and 12B are plots of shear modulus versus time for a plurality of materials that exhibit both rapid and slow dynamics, respectively. The data of FIGS. 12A and 12B demonstrates the ability of the disclosed methods to measure viscoelastic properties with sampling periods as short as 100 milliseconds or as long as 24 hours. For example, as illustrated in FIGS. 12A and 12B, the disclosed methods are capable of measuring and monitoring fast phase transitions such as ultraviolet crosslinking of polymers (i.e., on the order of seconds) and slow phase transitions such as genipin crosslinking of gelatin (i.e., on the order of days). In some examples, the identification of a discontinuity in frequency and a temporary elevation of damping are indicators of phase transition.

Figure 13A:
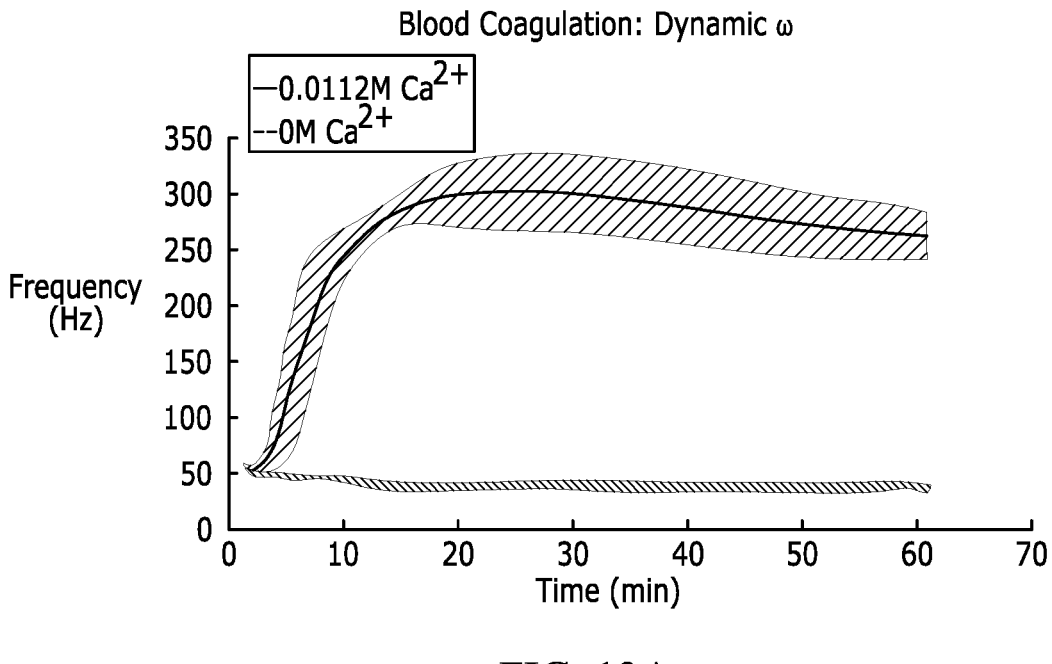
FIG. 13A is a plot of resonant frequency over time for porcine blood samples, in accordance with an example.
Figure 13B:
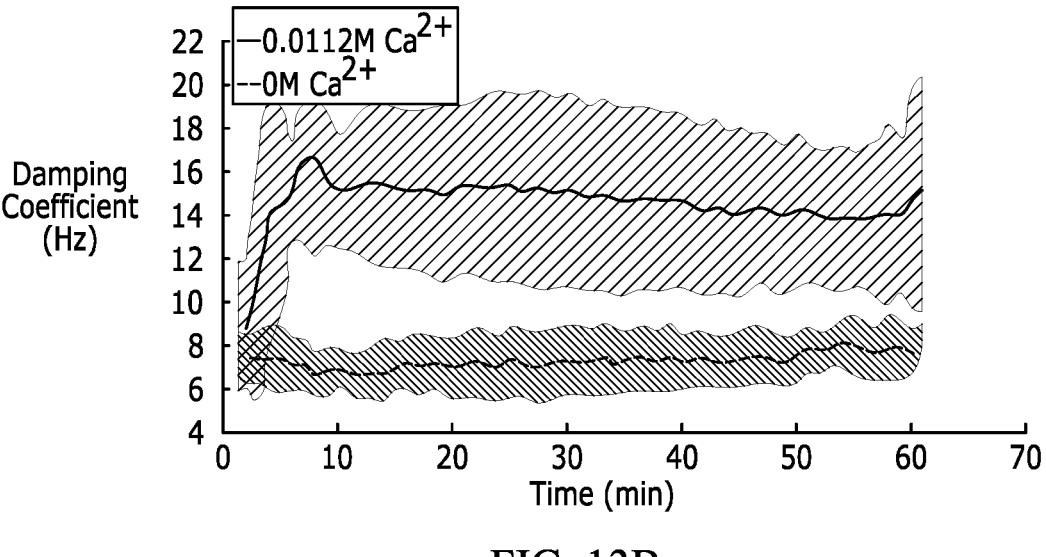
FIG. 13B is a plot of damping coefficient over time for porcine blood samples, in accordance with an example.

Dynamic changes of viscoelastic properties such as shear modulus and viscosity may be useful in diagnosis of coagulopathy, as well as for other applications across a variety of industries. FIGS. 13A and 13B are plots of a resonant frequency and damping coefficient over time for whole porcine blood as the sample 302. Coagulation of the porcine blood is initially inhibited by treating the blood with a citrate and then introducing calcium ions to the blood to initiate the clotting cascade while tracking with the present techniques. The resonant frequency and damping coefficient of the blood is then measured over a sampling period using the methods described herein. Both the dynamic resonant frequency and dynamic damping coefficient increases over time during coagulation of the porcine blood. The maximum resonant frequency is higher for the blood than the fibrin samples. While blood clots contain fibrin, a blood clot also contains platelets and additional enzymes, such as Factor XIII, that crosslink fibrin to further strengthen the clot. Therefore, it is expected that the frequencies and damping coefficients differ between the pure fibrin hydrogels as shown in FIGS. 11A and 11B and coagulating blood.

Figure 14:
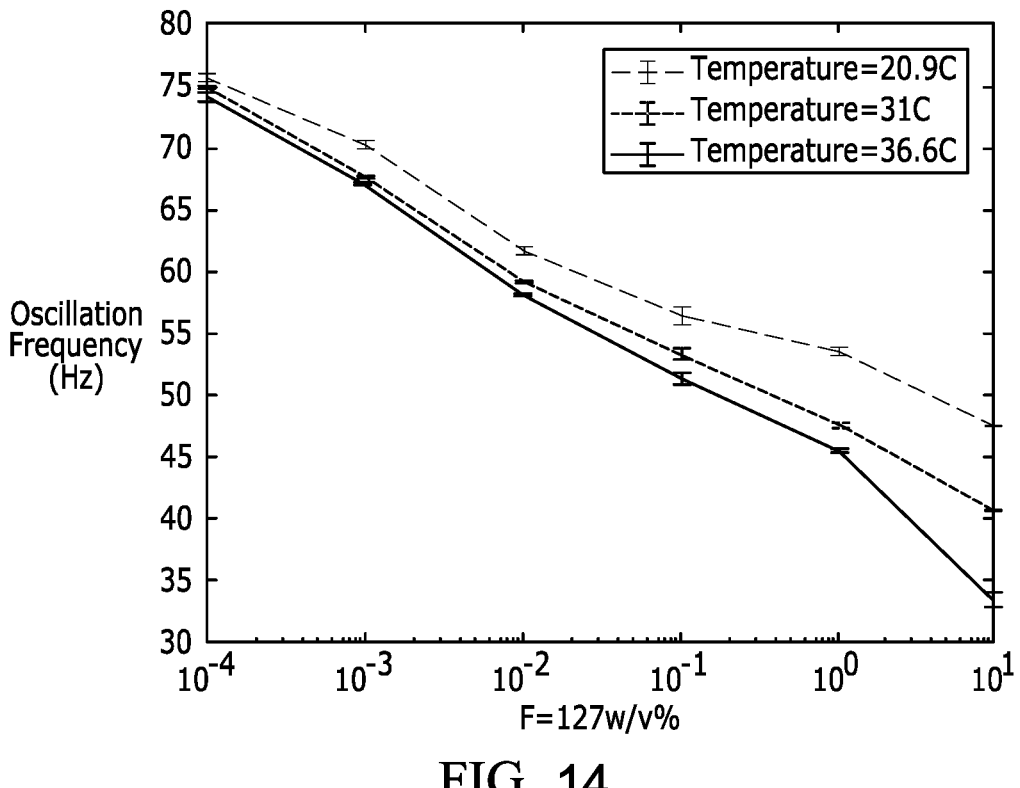
FIG. 14 is a plot of resonant frequency for a plurality of pluronic F-127 concentrations at various temperatures, in accordance with an example.

Measurements were performed to determine surface tension in aqueous solution using the described methods described herein. Deionized water with pluronic F-127 concentrations of between 0% to 10% w/v surfactant is used as the sample 302. FIG. 14 plots resonant frequency for different pluronic F-127 concentrations at various temperatures. FIG. 14 shows that the resonant frequency of the deionized water samples decreases with increased surfactant concentration. The trend of the decreasing trend of the resonant frequency is consistent with decreased surface tension, which reduces the restoring force of surface oscillations. In turn, the reduced restoring force reduces the resonant and oscillatory frequencies of the sample. Additionally, the resonant oscillatory frequencies of the sample decrease with increased temperature, which may be due to decreased surface tension at increased temperatures. FIG. 14 demonstrates the ability of the disclosed methods to measure surface energy at the interface of a sample.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the target matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A method for performing an acoustic rheology measurement, the method comprising:

providing, by a first ultrasound transducer, an excitation tone burst to a sample with a defined surface area, the sample in a cylindrical-shaped chamber well, the excitation tone burst being focused at a focal position at an interface of the sample and inducing a perturbation on the interface, the perturbation being characterized by an initial deformation or displacement of the interface followed by free oscillatory motion on the interface;

providing, by a second ultrasound transducer, a plurality of short pulses to the sample at the focal position, the plurality of pulses being confocal and collinear with the excitation tone burst and synchronized, in time, to impinge upon the interface after the excitation tone burst, to receive, from the interface, echoes responsive to the initial displacement and the following oscillatory motion of the interface;

detecting, by the second transducer, the echoes and providing electrical signals indicative of the echoes to a processor;

determining, by the processor, a displacement as a function of time of the interface from the detected echoes;

determining, by the processor, a frequency spectrum of the free oscillatory motion on the interface from the displacement as a function of time of the interface;

determining, by the processor, resonant properties of the interface, including a resonant oscillation frequency and damping of the interface, from the displacement as a function of time of the interface; and applying, by the processor, a hydrodynamic model and determining one or more viscoelastic properties of the sample or one or more intrinsic properties of the sample based on measured spectral properties of the interface.

2. The method of claim 1, wherein the resonant properties are selected from the group consisting of natural frequencies, maximum strains, and damping coefficients corresponding to various modes of surface oscillation.

3. The method of claim 1, wherein the one or more viscoelastic properties or the one or more intrinsic properties are selected from the group consisting of a shear modulus, a Young's modulus, a kinematic viscosity, a shear viscosity, and an interface energy.

4. The method of claim 1, wherein determining the displacement as a function of time of the interface of the sample comprises:

providing a plurality of the excitation tone bursts over a sampling time window;

detecting, by the second transducer, corresponding echoes in response to each of the excitation tone bursts;

determining, by the processor, the displacement as a function of time of the interface over the sampling time window; and determining, by the processor, changes in the one or more viscoelastic properties or the one or more intrinsic properties of the sample over the sampling time window.

5. The method of claim 4, wherein the plurality of excitation tone bursts are applied between every 10 ms to 100 ms.

6. The method of claim 4, wherein the plurality of excitation tone bursts are applied between every 100 ms.

7. The method of claim 1, wherein determining the displacement as a function of time of the interface of the sample comprises:

providing a plurality of the excitation tone bursts over a sampling time window;

detecting, by the second transducer, corresponding echoes in response to each of the excitation tone bursts;

determining, by the processor, the displacement as a function of time of the interface over the sampling time window; and determining, by the processor, one or more dynamic viscoelastic properties of the sample over the sampling time window.

8. The method of claim 7, wherein the one or more dynamic viscoelastic properties change due to processes selected from the group consisting of blood coagulation, plasma coagulation, hydrogel gelation, crosslinking of polymer chains, polymer hydrolysis, and proteolytic degradation.

9. The method of claim 7, wherein the one or more dynamic viscoelastic properties is selected from the group consisting of a transition of one or more physical properties of the sample, the one or more physical properties including at least one of a liquid phase state, a solid phase state, a kinetic gelation rate, a kinetic degradation rate, an initial viscoelastic state, a final viscoelastic state, and a gelation time.

10. The method of claim 7, further comprising:

generating, by the processor, a spectrogram or dynamic phase diagram from the one or more dynamic viscoelastic properties.

11. The method of claim 1, wherein the sample comprises one or more of a hydrogel selected from the group consisting of protein hydrogel, fibrin hydrogel, collagen hydrogel, gelatin hydrogel, silk fibroin hydrogel, polysaccharide hydrogel, agar hydrogel, agarose hydrogel, alginate hydrogel, hyaluronic acid hydrogel, heparin hydrogel, chitosan hydrogel, and cellulose hydrogel.

12. The method of claim 1, wherein the sample comprises one or more of a hydrogel selected from the group consisting of Polyethylene glycol (PEG) hydrogel, Polyethylene oxide (PEO) hydrogel, Polyacrylamide (PAM) hydrogel, Polymethacrylamide (PMAM) hydrogel, Poly-N-isopropyl acrylamide (PNIPAAm) hydrogel, Polyhydroxyethylmethacrylate (PHEMA) hydrogel, Polyvinylpyrrolidone (PVP) hydrogel, Polyvinyl alcohol (PVA) hydrogel, and Polyacrylic acid (PAA) hydrogel.

13. The method of claim 1, wherein the sample comprises one or more of a polymer selected from the group consisting of Polydimethylsiloxane (PDMS), Polymethylmethacrylate (PMMA), Polyvinyl chloride (PVC), Ethylene propylene rubber (EPR), Styrene butadiene rubber (SBR), Nitrile butadiene rubber (NBR), Thermoplastic polyurethane (TPU), and Polyisoprene (IR).

14. The method of claim 1, wherein the sample comprises one or more of a biological fluid selected from the group consisting of whole blood, plasma, serum, synovial fluid, mucus, lacrimal fluid, ascites fluid, interstitial fluid, gastric fluid, semen, sweat, pus, amniotic fluid, vaginal fluid, bile, cerebrospinal fluid, bronchoalveolar lavage fluid, and saliva.

15. The method of claim 1, wherein the sample comprises one or more of a tissue selected from the group consisting of connective tissue, muscle tissue, epithelial tissue, and nervous tissue.

16. The method of claim 1, wherein the sample comprises food.

17. The method of claim 1, wherein the sample comprises one or more cosmetics.

18. The method of claim 1, wherein the first transducer and second transducer are a single transducer.

19. The method of claim 1, wherein the cylindrical chamber well has a circular cross-sectional profile.

20. The method of claim 1, wherein the cylindrical chamber well has an elliptical cross-sectional profile.

21. The method of claim 1, wherein the cylindrical chamber well has tapered sides.

22. The method of claim 1, further comprising:

providing, by the second transducer, a plurality of ranging acoustic pulses to the sample and recording a plurality of ranging responsive echoes; and determining a location of the interface and the focal position at the interface from the ranging responsive pulse echoes.

23. The method of claim 22, further comprising:

determining, by the processor and based on the ranging responsive echoes, locations of edges of the cylindrical chamber well; and aligning, by one or more transducer mounts, one or more of the first transducer and the second transducer relative to the open cylindrical chamber well to ensure the focal position is on a geometric centerline of the open cylindrical chamber well.

24. The method of claim 19, wherein the first transducer and the second transducer are spaced below the open cylindrical chamber well so as to not physically contact the open cylindrical chamber well or the sample, and such that the first transducer and the second transducer provide the excitation tone burst and the pulses, respectively, through a bulk region of the sample.

25. A system for performing an acoustic rheology measurement, the system comprising:

a first transducer aligned to provide an excitation tone burst to a sample in a cylindrical-shaped chamber well and to focus the excitation tone burst at a focal position at an interface of the sample for inducing an interface perturbation on the interface, the interface perturbation being characterized by an initial displacement on the interface followed by free oscillatory motion on the interface;

a second transducer configured to provide a plurality of pulses to the sample at the focal position and confocal and collinear with the excitation tone burst, the second transducer further configured to synchronize the plurality of pulses to impinge upon the interface after the excitation tone burst, the second transducing being further configured to detect echoes from the interface and to provide electrical signals indicative of the detected echoes to one or more processors of the system; and a non-transitory computer-readable memory coupled to the one or more processors and storing instructions thereon that, when executed by the one or more processors, cause the one or more processors to:

determine a displacement as a function of time of the interface from the detected echoes;

determine resonant properties of the sample from the displacement as a function of time of the interface; and apply the resonant properties to a hydrodynamic model and determine one or more viscoelastic properties of the sample or one or more intrinsic properties of the sample.

* * * * *